(12) United States Patent
    Xue et al.

(10) Patent No.: US 10,852,287 B2
(45) Date of Patent: Dec. 1, 2020

(54) IN-SITU PASSIVE SAMPLING DEVICE BASED ON PHYSICAL AND CHEMICAL AND BIO-COUPLING MONITORING AND APPLICATION

(71) Applicants: Changzhou Environmental Monitoring Center, Changzhou (CN); Nanjing Institute of Environmental Sciences Ministry of Environmental Protection, Nanjing (CN); Changzhou University, Changzhou (CN)

(72) Inventors: Yingang Xue, Changzhou (CN); Xiaofei Zhang, Nanjing (CN); Xia Xu, Changzhou (CN); Aiguo Zhang, Nanjing (CN); Deyang Kong, Nanjing (CN); Jiaquan Teng, Changzhou (CN)

( * ) Notice: Subject to any disclaimer, the term of this patent is extended or adjusted under 35 U.S.C. 154(b) by 183 days.

(21) Appl. No.: 16/253,233

(22) Filed: Jan. 22, 2019

(65) Prior Publication Data
    US 2020/0096483 A1   Mar. 26, 2020

(51) Int. Cl.
    *G01N 33/18*    (2006.01)
    *A01K 63/00*    (2017.01)

(52) U.S. Cl.
    CPC .......... *G01N 33/186* (2013.01); *A01K 63/00* (2013.01); *G01N 33/1826* (2013.01); *A01K 63/006* (2013.01)

(58) Field of Classification Search
    CPC .......... G01N 33/1826; G01N 33/1833; G01N 33/186; G01N 33/1886; G01N 2033/184; A01K 63/00; A01K 63/003; A01K 63/006
    See application file for complete search history.

(56) References Cited

U.S. PATENT DOCUMENTS

| | | | |
|---|---|---|---|
| 4,744,331 A * | 5/1988 | Whiffin | A01K 29/00 119/223 |
| 6,119,630 A * | 9/2000 | Lobsiger | G01N 33/1886 119/238 |
| 7,591,979 B2 * | 9/2009 | Hill | G01N 1/14 422/62 |
| 8,805,618 B2 * | 8/2014 | Andersen | G01N 33/1886 702/13 |
| 9,776,692 B2 * | 10/2017 | Merz | G01N 33/186 |

\* cited by examiner

*Primary Examiner* — Justin N Olamit
(74) *Attorney, Agent, or Firm* — W&K IP

(57) ABSTRACT

The invention discloses an in-situ passive sampling device based on physical and chemical and bio-coupling monitoring and use thereof, the device comprises a foam plastic tray on the water surface, a supporting connection device under the water surface, a fish farming device and a sampling device. The invention comprises three passive samplers and a fish farming device, wherein the fish farming device can ensure the survival environment of the fish in the long-term test, maintain the fish survival rate, and apply the device to the safety evaluation of water quality of the centralized drinking water source.

8 Claims, 4 Drawing Sheets

IN-SITU PASSIVE SAMPLING DEVICE BASED ON PHYSICAL AND CHEMICAL AND BIO-COUPLING MONITORING AND APPLICATION

CROSS-REFERENCE TO RELATED APPLICATIONS

This application claims priority to Chinese Patent Application No. 201811046616.7 with a filing date of Sep. 21, 2018. The content of the aforementioned applications, including any intervening amendments thereto, are incorporated herein by reference.

TECHNICAL FIELD

The invention belongs to the technical field of environmental protection, and particularly relates to an in-situ passive sampling device based on physical and chemical and bio-coupling monitoring and application.

BACKGROUND

Drinking water safety is an important issue related to people's livelihood and stability, it is an important indicator of the development level and life quality of a country and regions, and an important indicator for achieving a well-off society. With the comprehensive implementation of the "Sanitary Standard for Drinking Water" (GB 5749-2006) across the country, the issue of drinking water safety has once again become a hot spot in public opinion. As early as January 2008, Jiangsu Province promulgated the "Decision of the Standing Committee of the People's Congress of Jiangsu Province on Strengthening the Protection of Drinking Water Sources." In March 2009, Measures for the Hygiene Monitoring and Management of the Centralized Drinking Water in the Rural Areas of Jiangsu Province was introduced with respect to the centralized drinking water in the rural areas, to continuously strengthen the supervision of drinking water safety work.

With the rapid development of the economy and society, the safety of drinking water is still not optimistic. Although the concentration of organic toxics in drinking water is generally low, people will expose to it through this life and it is imperative to understand the level and harm of contaminants in drinking water, and take preventive measures.

Therefore, at present, China's environmental monitoring systems mostly use instantaneous samples based on a certain frequency to understand the water quality. It takes more time and money to collect and process large-volume of water samples, and representative problems of sampling attract attention. In addition, these methods measure the "full amount" of the dissolved state and adsorbed state attached to the particulate matter in water, wherein the dissolved organic contaminant is directly bioavailable. There is no distinction between morphology (dissolved or adsorbed), no concern about the biological effects of organic toxics at low concentrations and long-term enrichment hazards, which need to be further improved in future work.

Passive sampling technology is a sampling technology that can simulate the biological activity in the environment containing chemical contaminants, which is simple, non-expendable, and non-hazardous. It can perform sampling for environmental monitoring in a wide range and for a long time, which effectively control the changing trend of environmental pollution.

It mainly includes three techniques: SPMD, POLICS and DGT:

(1) The main structure of SPMD comprises a sleeve made of a thin strip of polyethylene film or other non-polar low density polymer film (low-density polyethylene, LDPE, of wall thickness 70~90 μm), the sleeve is equipped with a thin layer of large molecular weight (>600 Da) neutral lipids (such as glycerol trioleate). SPMD allows dissolved non-polar/weak polar molecules in water to pass through the pores of the polymer membrane and into the device in a passive diffusion mode and gradually combine with neutral lipids, while those contaminants attached to the water particles and combined to the dissolved organic carbon (such as humic acid) cannot enter the SPMD due to their volume limitations. The organic contaminants entering the SPMD can be quantitatively dialyzed and separated by means of shaking with organic solvents, microwave assistance, ultrasonic assistance, accelerated solvent extraction assistance and the like, and then purified by means including osmotic gel chromatography to achieve the time accumulative collection and quantification of organic contaminants to the environment.

(2) POCIS (Polar Organic Chemical Integrative Sampler) semi-permeable membrane sampling equipment simulates aquatic biological respiratory exposure system, collecting water-soluble (polar or hydrophilic) organic substances in water, which can be applied to toxicity evaluation and toxicity identification evaluation (TIE).

(3) DGT (Thin Diffusion Gradient Technology), DGT device is simple, can set the enrichment sampling time within a certain time range, can enrich multiple elements at the same time, and can provide accumulation content and average concentration values, following the concentration fluctuation of metal ions in the bulk solution during the enrichment time, are especially useful for total analysis of trace systems with large fluctuations in concentration and in situ enrichment of trace systems.

It can be seen that the three passive sampling techniques have their own advantages in physical and chemical detection, however all three techniques are lacking in microbial community analysis, microbial testing and bio-enrichment. Micro-biological community exist objectively in aquatic ecosystems. In the level of biological formation, the community level is higher than the species and population level. Therefore, the biological monitoring and toxicity tests at the community level are more environmentally authentic than the species and population levels, providing the environmental management department with structural and functional parameters that conform to the objective environment, so as to make scientific judgments. The microbiological test is mainly to analyze various potential pathogenic microorganisms in water body, and to test and analyze the microbiological safety of natural water body and drinking water. Bio-enrichment is a representation of the extent of pollution in rivers and its impact on fish-eating animals and humans by providing levels of bio-enriched contaminants in the body.

In view of this, there is a need for a sampling device that can be applied to the safety evaluation of water quality in centralized drinking water sources, to evaluate the long-term cumulative effects of contaminants, and to be closer to the actual conditions of the biological exposure environment, especially in emergencies. Provide evidence of evaluation of the background and long-term environmental changes at the time, increase the credibility of environmental pollution judgments, and provide effectiveness of pre-existing monitoring, early warning and post-contamination tracking on environmental pollution cases.

SUMMARY OF THE INVENTION

In view of the above technical problems, the present invention provides an in-situ passive sampling device capable of simultaneously monitoring biological community survey, fish toxicity test, microbial test and fish tissue contaminants residue analysis.

The technical solution of the present invention is: an in-situ passive sampling device based on physical and chemical and bio-coupling monitoring, comprising an upper unit and a lower unit.

The upper unit comprises a foam plastic tray floating on the water surface, a bracket on the foam plastic tray, the bracket is detachably fixed on the foam plastic tray by bolts, and a power supply device, a microcontroller, and a suction pump and an automatic feeding box on the bracket, wherein the power supply device respectively supplies power to the suction pump and the automatic feeding box, and the microcontroller is used for timing switch control of the suction pump and the automatic feeding box.

The lower unit comprises a support connecting device, a fish farming device and a sampling device, the support connecting device comprises a central post, a connecting rod, a feed pipe and a plastic hose, and the upper surface of the central post is connected to the lower bottom surface of the foam plastic tray by 2-4 cables, the central post is internally provided with a longitudinal through passage, the lower end of the plastic hose is screwed to the upper end of the through passage, the upper end extends upward and penetrates the foam plastic tray, and connected to the outlet of the suction pump and the outlet of the automatic feeding box respectively through the manifold, the upper end of the feed pipe is screwed to the lower port of the through passage, the middle and lower parts of the feed pipe are provided with external threads, and the connecting rods are provided in three in total, and the proximal ends of the rods are detachably connected to the side walls of the central post by bolts, respectively.

The fish farming device comprises a fishbox body and a fishbox cover, wherein the fishbox cover and the fishbox body are screwed into a spherical structure, the top of the fishbox cover is provided with a thread hole, and a plurality of through holes are provided around the thread hole, the thread hole is fitted connected with the external thread of the feed pipe, and the end of the feed pipe is extended to the inside of the fishbox body, and the fry, which is generally carp fry are placed inside the fishbox body.

The sampling device comprises a first fixing frame, a second fixing frame, and a third fixing frame, the top of the first fixing frame, the second fixing frame and the third fixing frame are respectively connected to the respective distal end of the three connecting rods by a lock, wherein the first fixing frame is provided with a thin film diffusion gradient passive sampler, the second fixing frame is provided with a semipermeable membrane passive sampler, and the third fixing frame is provided with a polar organic compound integrated sampler.

Further, the power supply device comprises a battery, an inverter, and a solar panel, the solar panel is obliquely disposed at a top of the bracket, and the inverter is connected between the solar panel and the battery for converting direct current into alternating current, and the battery supplies the stored alternating current to the device to be powered.

Further, the foam plastic tray is made of PFU, which on the one hand can provide buoyancy, and on the other hand when PFU are soaked in water, after exposure for a certain period of time, most of the micro-organisms in the water body can be clustered into the PFU, and the extruded water sample can represent the micro-biological community in the water body. This method is called PFU micro-biological community monitoring method (referred to as PFU method), which collects micro-biological community in the water body using foam plastic blocks as artificial matrix, and determine various parameters of the structure and function of the community to evaluate water quality. In addition, the indoor toxicity test method is used to predict the toxicity intensity of industrial wastewater and chemicals on micro-biological community in the receiving water body, and propose a community-level reference for the development of the safe concentration and the maximum allowable concentration.

Further, a plurality of LED lights are embedded in the bottom of the central post for providing sufficient illumination for the fry during the test.

Still further, a waterproof cable juxtaposed with the cable is disposed between the central post and the foam plastic tray, and the waterproof cable is electrically connected to the battery and the microcontroller upwardly, and supplies power to the LED lamp downward. The waterproof cable has good stability and can work in the water for a long time.

Further, the fishbox body is provided at the bottom with a mesh, and a filler layer is provided on the mesh, wherein the filler layer is planted with aquatic plants, and the filler layer is a ceramsite having a particle diameter of 0.5-1 cm.

Further, a plurality of staggered strip grooves are formed in the side wall of the fishbox body to facilitate mutual exchange of water in the fishbox body and external water.

Still further, the fish farming device further comprises a sink, the inner bottom of the sink is fixedly connected to the bottom of the fishbox body through a connecting rod, and the upper edge of the sink is higher than the highest position of the strip groove, the sink is used to store water, and it is necessary to maintain a certain amount of water before and after the test to ensure the survival of the fish.

The invention also provides use of an in-situ passive sampling device based on physical and chemical and bio-coupling monitoring, the sampling device is used for in-situ biological monitoring of drinking water sources, and the biological monitoring content includes biological community, toxicity test, microbial test and residues of contaminants in fish tissues.

The working method of the invention comprises the following steps:

Assembling device: connecting a foot of the bracket by a bolt to the upper surface of the foam plastic tray, and the battery is mounted with a fully charged battery, an inverter, a solar panel, a microcontroller, a suction pump, and an automatic feeding box with sufficient feed, connecting the lower end of the plastic hose to the upper end of the through passage of the central post through a thread joint, running the upper end of the plastic hose through the foam plastic tray, and connecting respectively with the outlets of the suction pump and the automatic feeding box through the manifold; running the waterproof cable connected to the LED light at the bottom of the central post upward through the foam plastic tray and connecting to the battery and the microcontroller for timing control of the LED light switch and it lumination duration; tying 2-4 cables between the central post and the foam plastic tray. The central post is provided at side walls with three clamping plate slots. The upper ends of the three connecting rods are respectively bolted to the three clamping plate slots. The angle between the connecting rod and the central post is 30-45 degrees, and then the first fixing frame, the second fixing frame and the third fixing frame are respectively connected to the lower ends of the three connecting rods by locks, and the film diffusion gradient passive sampler, the semi-permeable membrane passive sampler and the polar organic compound integrated sampler are sequentially fixed to the first fixing frame, the second fixing frame and the third fixing frame through the fixing clips respectively. Placing a filler layer at the bottom of the fishbox body and growing the aquatic plants, filling with clean water and 4-6 carp fry, screwing the fishbox cover over the fishbox body, and bring to the detection site. After reaching the detection site, pouring out the clear water in the fishbox body, and replacing with a small amount of water to be detected, and connecting with the thread hole of the fishbox cover to the feed pipe which communicates with the through passage.

Detection method: placing the whole device in the detection water source with the foam plastic tray floating on the water surface, and fixed by the sling, subjecting the fishbox body to internal aerate by controlling the suction pump using the micro-control device at an interval of 3-5 h for 30-40 min to supply oxygen to the carp, meanwhile accelerating the water circulation; quantitative transferring the feed to the fishbox body by controlling the automatic feeding box using the microcontroller at an interval of 12-24 h, meanwhile turning the suction pump on, to transfer the feed by the airflow assistance and prevent clogging; controlling the LED light using the microcontroller to supplement light to the fishbox body for 5-6 hours every day, and taking the device out after 30 days.

Compared with the prior art, the present invention has the beneficial effects that the present invention comprises three passive samplers and a fish farming device, wherein the fish farming device can ensure the survival environment of the fish in the long-term detection and maintain the fish survival rate. rate. The foam plastic tray of the present invention is made of PFU, which can provide buoyancy on the one hand, and on the other hand when PFU are soaked in water, after exposure for a certain period of time, most of the micro-organisms in the water body can be clustered into the PFU, and the extruded water sample can represent the micro-biological community in the water body. In addition, PFU can be equivalent to a biofilm. After a long time, many microorganisms will be attached to it. After DNA extraction, qPCR and high-throughput sequencing technologies, it can be used to study the microbial ecology of drinking water. The long-term cumulative effect of contaminants can be evaluated with the application of the present device to the water quality safety evaluation of centralized drinking water sources, which is closer to the actual situation of the biological exposure environment, especially in the case of sudden environmental pollution incidents, and can provide evidence of evaluation for the background and long-term environmental changes, increase the credibility of environmental pollution evaluation, and play effectiveness of pre-monitoring, early warning and post-contamination tracking for environmental pollution cases.

DRAWINGS OF THE INVENTION

Among them, 1—foam plastic tray, 2—bracket, 3—power supply, 31—battery, 32—inverter, 33—solar panel, 4—microcontroller, 5—suction pump, 6—automatic feeding box, 7—support connecting device, 71—central post, 710—through passage, 72—connecting rod, 73—feed pipe, 74—plastic hose, 75—LED lamp, 8—fish farming device, 81—fishbox body, 82—fishbox cover, 83—thread hole, 84—through hole, 85—fish, 86—mesh, 87—filler layer, 88—aquatic plant, 89—striped groove, 810—sink, 811—connected rod, 9—sampling device, 91—first fixing frame, 92—second fixing frame, 93—third fixing frame, 94—lock, 95—film diffusion gradient passive sampler, 96—semi-permeable membrane passive sampler, 97—polar organic compound integrated sampler, 10—cable, 11—manifold, 12—waterproof cable.

DETAILED DESCRIPTION

Figure 1:
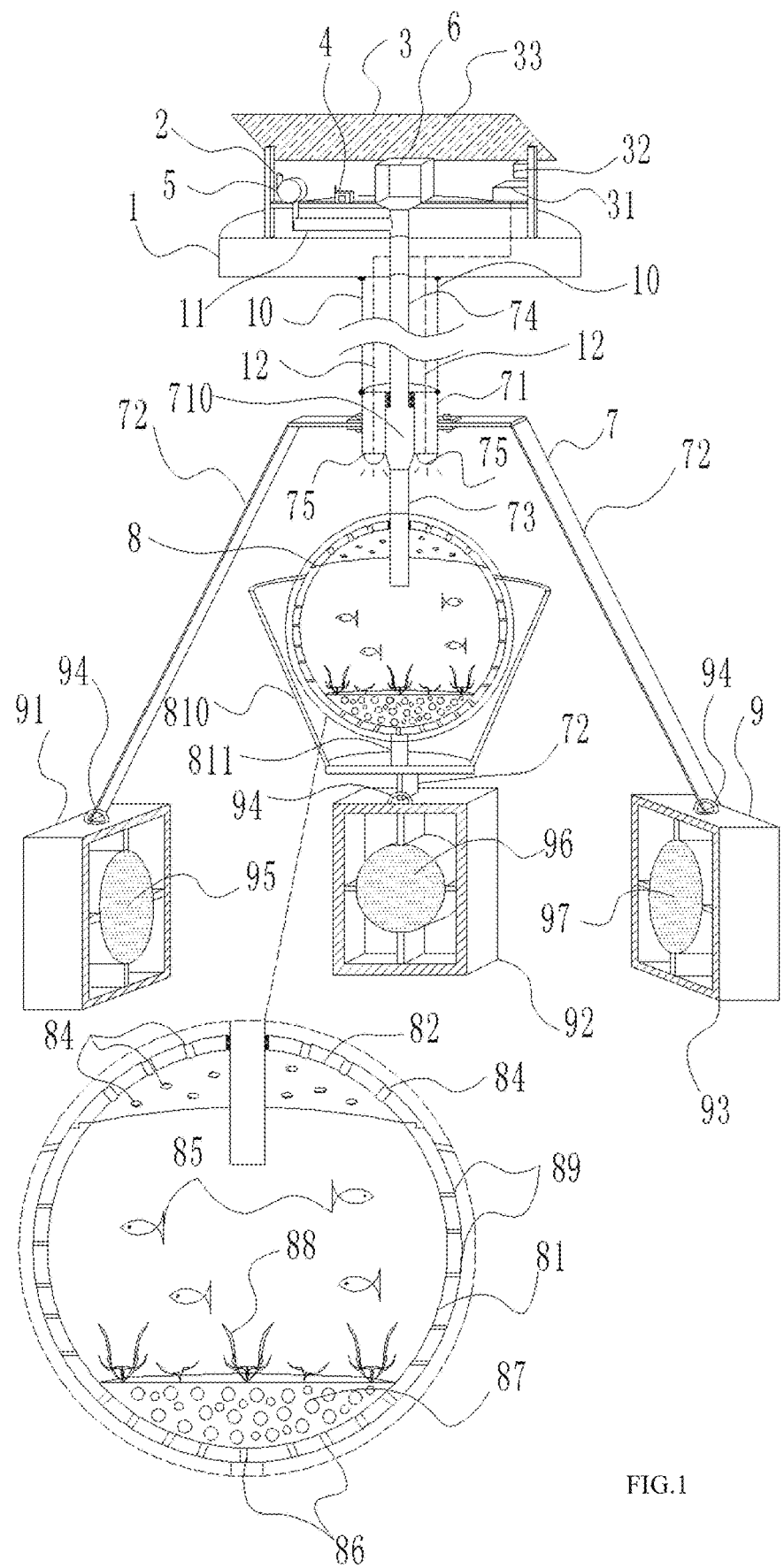
FIG. 1 is a schematic view of the overall structure of the present invention.

As shown in FIG. 1, an in-situ passive sampling device based on physical and chemical and bio-coupling monitoring comprises an upper unit and a lower unit, and the upper unit comprises a foam plastic tray 1 floating on the water surface, wherein the material of the foam plastic tray 1 is PFU, which on the one hand can provide buoyancy, and on the other hand when PFU are soaked in water, after exposure for a certain period of time, most of the micro-organisms in the water body can be clustered into the PFU, and the extruded water sample can represent the micro-biological community in the water body. PFU can also be used as a biofilm. After a long time, many microorganisms will be attached to it. After DNA extraction, qPCR and high-throughput sequencing technologies, it can be used to study the microbial ecology of drinking water. The upper unit further comprises a bracket 2 on the foam plastic tray 1, the bracket 2 is detachably fixed to the foam plastic tray 1 by bolts, and a power supply 3, a microcontroller 4, a suction pump 5 and an automatic feeding box 6 on the bracket 2, the power supply 3 supplies power to the suction pump 5 and the automatic feeding box 6 respectively, the microcontroller 4 is used for timing switch control of the suction pump 5 and the automatic feeding box 6; the power supply 3 comprises a battery 31, an inverter 32 and a solar panel 33, the solar panel 33 is inclined at the top of the bracket 2, and an inverter 32 is connected between the solar panel 33 and the battery 31 for converting direct current into alternating current, and the battery 31 supplies the stored alternating current to the electric device.

As shown in FIG. 1, the lower unit includes a support connecting device 7, a fish farming device 8, and a sampling device 9. The support connecting device 7 comprises a central post 71, a connecting rod 72, a feed pipe 73, a plastic hose 74, and an upper surface of the central post 71 is connected to a lower bottom surface of the foam plastic tray 1 by two cables 10, as shown in FIG. 1, and a plurality of LED lamps 75 are embedded in the bottom of the central post 71 for providing sufficient illumination for the fry during the test. A waterproof cable 12 juxtaposed with the cable 10 is disposed between the central post 71 and the foam plastic tray 1. The waterproof cable 12 is electrically connected upwardly to the battery 31 and the microcontroller 4, and supplies power downward to the LED lamp 75. The waterproof cable 12 has good stability and can work in water for a long time. The central post 71 is internally provided with a longitudinal through passage 710. The lower end of the plastic hose 74 is screwed to the upper end of the through passage 710, and the upper end extends upwardly and penetrates through the foam plastic tray 1, connects through the manifold 11 to the outlet of the suction pump 5 and the outlet of the automatic feeding box 6 respectively, the upper end of the feed pipe 73 is screwed to the lower port of the through passage 710, the middle and lower parts of the feed pipe 73 are provided with external threads, and the connecting rods 72 are provided in three in total, and the proximal ends of the connecting rods 72 are detachably connected to the side walls of the central post 71 respectively by bolts.

Figure 2:
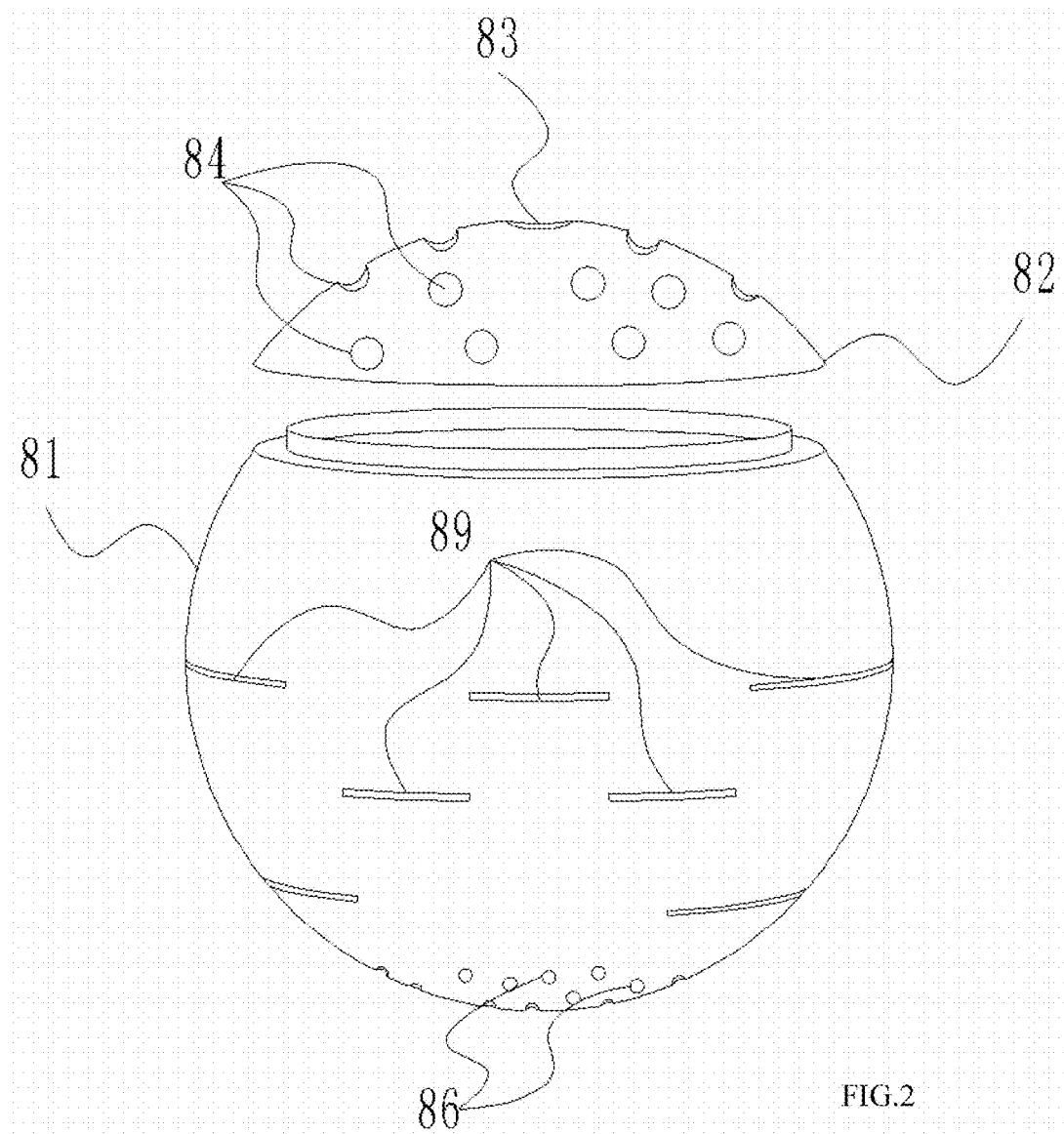
FIG. 2 is a schematic view showing the split structure of the fishbox cover and the fishbox body of the present invention.

As shown in FIG. 1-2, the fish farming device 8 comprises a fishbox body 81 and a fishbox cover 82. The fishbox cover 82 and the fishbox body 81 are screwed into a spherical structure, and the fishbox cover 82 is provided at the top with a screw hole. 83. A plurality of through holes 84 are provided around the thread hole 83. The thread holes 83 are fitted to the external threads of the feed pipe 73, and the ends of the feed pipes 73 are extended to the inner of the fishbox body 81, and internal of the fishbox body 81 is provided with fry 85 which is generally carp fry. As shown in FIG. 1, the bottom of the fishbox body 81 is provided with a mesh 86. The mesh 86 is provided with a filler layer 87, and the filler layer 87 is planted with aquatic plants 88, and the filler layer 87 is a ceramsite having a particle size of 1 cm. A plurality of staggered strip grooves 89 are formed in the side wall of the fishbox body 81 to facilitate mutual exchange of water in the fishbox body 81 and external water. The fish farming device 8 further comprises a sink 810. The inner bottom of the sink 810 is fixedly connected to the bottom of the fishbox body 81 through a connecting rod 811, and the upper edge of the sink 810 is higher than the highest position of the strip groove 89, and the sink 810 is used for water storage, it is necessary to maintain a certain amount of water before and after the test to ensure the survival of fish.

As shown in FIG. 1, the sampling device 9 comprises a first fixing frame 91, a second fixing frame 92, and a third fixing frame 93. The tops of the first fixing frame 91, the second fixing frame 92, and the third fixing frame 93 respectively connected to the respective distal end of the three connecting rods 72 by the lock 94. Wherein, the first fixing frame 91 is provided with a thin film diffusion gradient passive sampler 95, and the second fixing frame 92 is provided with a semipermeable membrane passive sampler 96. A polar organic compound integrated sampler 97 is provided in the third fixing frame 93. The sampling device is used for in-situ biological monitoring of drinking water sources, including biological community, toxicity tests, microbial tests, and contaminant residues in fish tissues.

The device is used to test the water collection well of Water Plant in Wei Village in Changzhou City, Jiangsu Province, with a detection period of 30 days.

The operation method of this embodiment comprises the following steps:

(1) Assembling device: the foot of the bracket 2 is bolted to the upper surface of the foam plastic tray 1. The bracket 2 is mounted with a fully charged battery 31, an inverter 32, a solar panel 33, a microcontroller 4, a suction pump 5 and an automatic feeding box 6 filled with sufficient feed, the lower end of the plastic hose 74 is connected to the upper end of the through passage 710 of the central post 71 through a thread joint, and the upper end of the plastic hose 74 passes through the foam plastic tray 1, and is connected to the outlet of the suction pump 5 and the automatic feeding box 6 respectively through the manifold 11; the waterproof cable 12 connected to the LED lamp 75 at the bottom of the central post 71 extends upward through the foam plastic tray 1 and is connected to the battery 31 and the microcontroller 4, for timing control of the switch and illumination duration of the LED lamp 75; the two cables 10 are tethered between the central post 71 and the foam plastic tray 1. The side wall of the central post 71 is provided with three clamping plate slots, and the upper ends of the three connecting rods 72 are respectively connected with the three clamping plate slots by bolts, and the angle between the connecting rod 72 and the central post 71 is 30 degrees, and then the first fixing frame 91, the second fixing frame 92, and the third fixing frame 93 are respectively connected to the lower ends of the three connecting rods 72 through the lock 94, the film diffusion gradient passive sampler 95, the semipermeable membrane passive sampler 96, and the polar organic compound integrated sampler 97 is sequentially fixed in the first fixing frame 91, the second fixing frame 92, and the third fixing frame 93 by fixing clips. The fishbox body 81 is provided at the bottom with the filler layer 87 and has the aquatic plant 88 planted, filled with clear water and four carp fry, and the fishbox cover 82 is screwed onto the fishbox body 81, and taken to the detection site, the fresh water in the fishbox body 81 is poured out when reaching the detection site, and replaced with a small amount of water to be detected, and the thread hole 83 of the fishbox cover 82 is connected to the feed pipe 73 that communicates with the through passage 710.

(2) Collecting Sample: The whole device is placed in the water source to be detected. The foam plastic tray 1 is allowed to float on the water surface and is fixed by the sling. The foam plastic tray 1 is used to sample with respect to three surface water body in the Taihu estuary area (DB1 DB2, DB3) for long time (30 days), PFU foam plastic tray 1 acts as a biofilm for the enrichment of surface water body microbes, when the PFU surface is enriched with a certain amount of microbes, the PFU material used for the foam plastic tray acts as a biofilm for the enrichment of surface water body microbes, the microcontroller 4 controls the suction pump 5 to aerate the inner fishbox body 81 for 45 min every 4 h to supply oxygen to the carp, and meanwhile accelerate the circulation of the water; the feed is quantitatively transfer to the inner of the fishbox body 81 by controlling the automatic feeding box 6 using the microcontroller 4, and at the same time, the suction pump 5 is turned on, and the feed is transferred by the airflow assistance to prevent clogging; the LED controller 75 is controlled by the microcontroller 4 to it luminate the fishbox body 81 with light for 5 h every day, and the device is taken out after 30 days.

Test Example 1: Study of the Microbial Community Structure of Water (1) DNA extraction: The surface of the foam plastic tray 1 was rinsed with sterile water, and the washed water sample was used for DNA extraction. According to the Omega Water DNA Kit instructions, the DNA is extracted from the rinse water sample, and after DNA extraction, the extracted DNA are measured for the concentration and purity of by NanoDrop2000 ultra-micro protein nucleic acid analyzer, and then stored at −20° C. for subsequent PCR amplification.

(2) PCR amplification: The extracted DNA product was subjected to PCR amplification using a 16S rDNA V4 region primer (515F/806R). The PCR amplification system totals 20 μL, containing 4 μL of 5× FastPfu buffer, 2 μL of dNTPs (2.5 mmol·L−1), 0.8 μL of forward primer (5 μmol·L−1), and 0.8 μL of reverse primer (5 μmol·L−1), 0.4 μL of FastPfu polymerase, 10 ng of DNA template, supplemented with ultrapure water to 20 μL. PCR amplification process: pre-denaturation at 95° C. for 2 min, denaturation at 95° C. for 30 s, reaction at anneal temperature of 55° C. for 30 s, extension at 72° C. for 90 s, for a total of 25 cycles, and finally extension at 72° C. for 10 min. The PCR product was electrophoresed using a ρ=2% agarose gel, and the product was recovered using Qiagen Gel Extraction Kit from the target band.

(3) High-throughput sequencing: The purified product was subjected to high-throughput sequencing and analysis via Hiseq PE250 platform. Library construction was performed using TruSeq® DNA PCR-Free Sample Preparation Kit Library, which was used to evaluate the quality of the sequencing library using Qubit 2.0 fluorometer and Agilent Bioanalyzer 2100 system.

(4) Data analysis: The operation classification unit (OTU) is divided according to the Uparse software, the sequence with ≥97% similarity is assigned to the same OTU, and the representative sequence of each OTU is screened to compare with the Silva database for species annotation analysis (threshold is set to 0.8~1). In order to study the phylogenetic relationships of different OTUs and the differences in dominant species in different samples, Muscle software was used for multiple sequence alignments.

Figure 3:
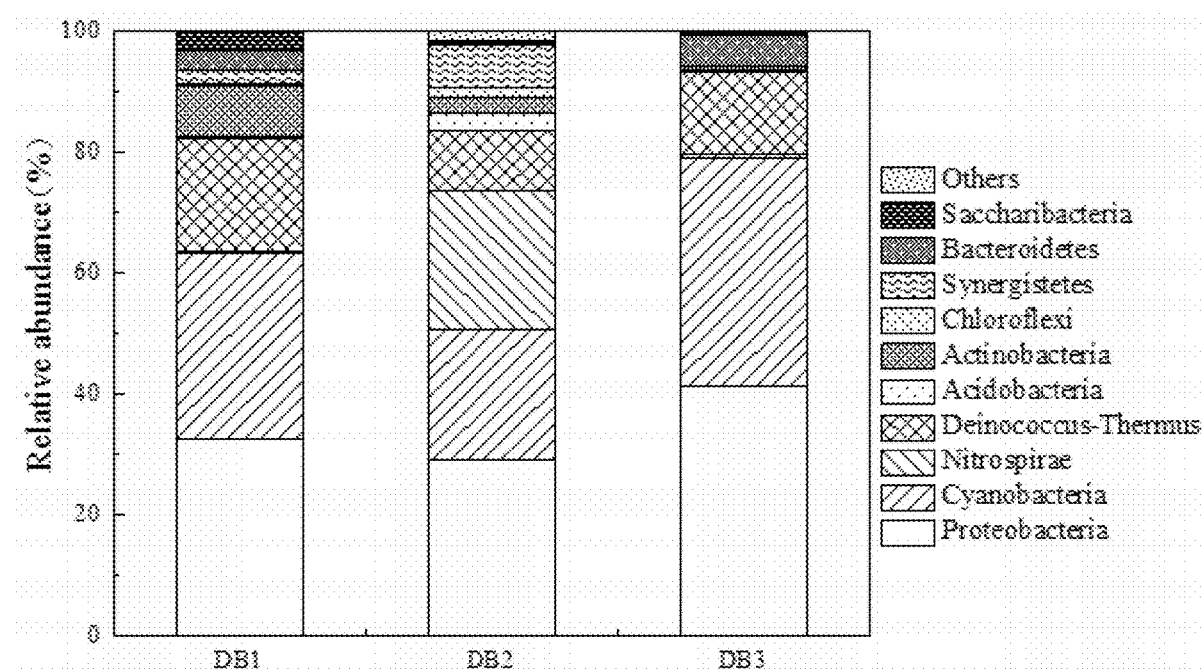
FIG. 3 is a horizontal dominant bacterial group in the surface water body of the estuary area of Taihu in the embodiment of the present invention.

Experimental results analysis: The surface water body of the Taihu estuary area was enriched and sampled for a long time by the sampling device, and the high-throughput sequencing was used to study the microbial community structure of the water. It can be seen from FIG. 3 that the dominant bacterial groups in the surface water body of Taihu include Proteobacteria (34.24%), Cyanobacteria (30.06%), Nitrospirae (7.85%), Deinococcus-Thermus (14.22%) and Acidobacteria (1.12%), the relative abundance of the remaining bacterial groups were less than 1%. Through the long-term monitoring of surface water body in the Taihu estuary area, it can be seen that Proteobacteria and Cyanobacteria are the two most dominant groups in the water community of the region, and the high abundance of Cyanobacteria deserves attention.

Figure 4:
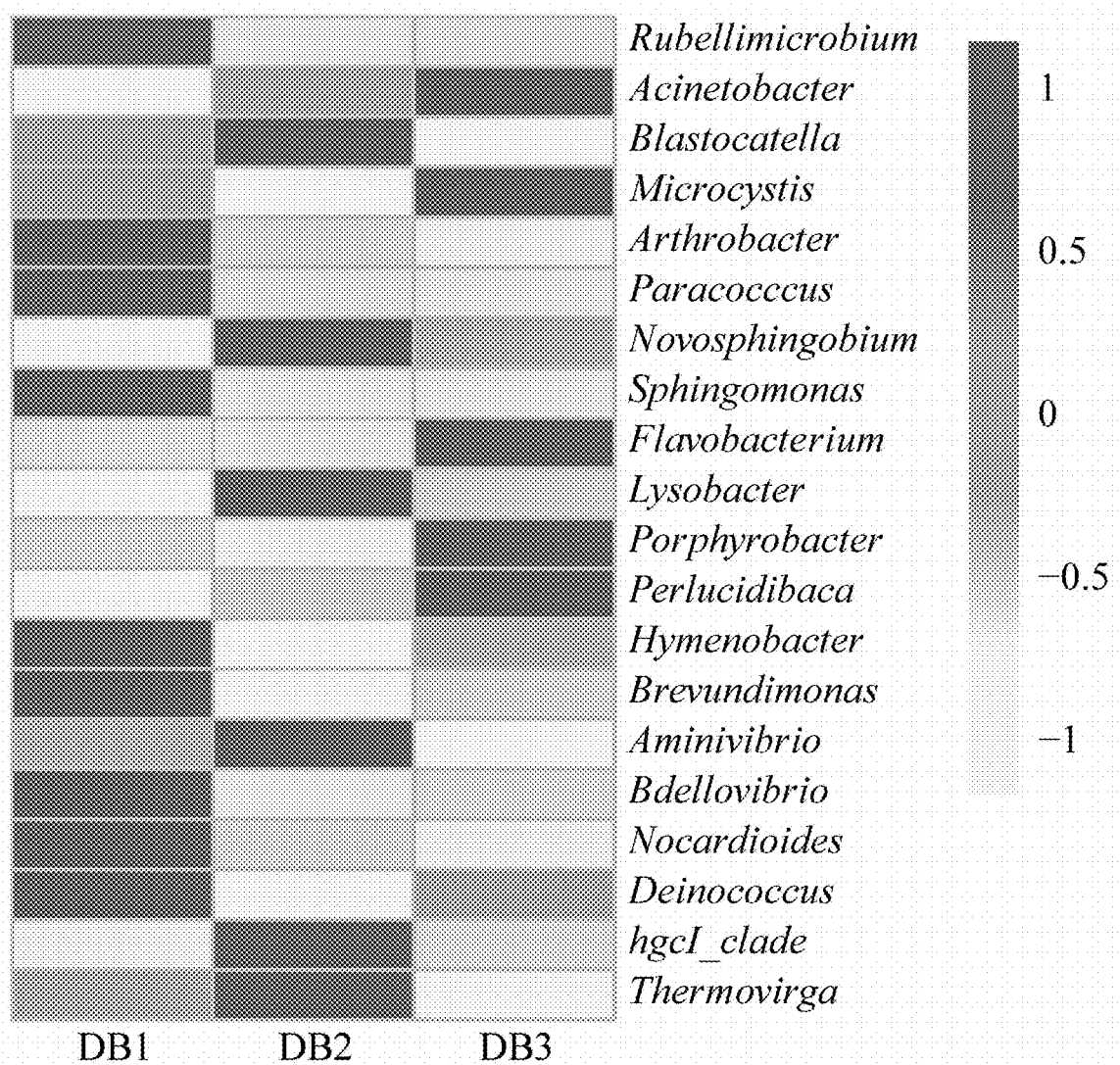
FIG. 4 is a horizontal bacterial community structure of surface water body in the estuary area of Taihu in the embodiment of the present invention.

According to the bacterial community structure, the surface water body in the Taihu estuary area are divided. FIG. 4 is a horizontal bacterial community structure spectrum. It can be seen that the abundance of dominant bacteria is different among the three sampling points, and the bacteria groups with higher relative abundance are Microcystis (22.12%), Deinococcus (14.18%), Acinetobacter (7.32%), Porphyrobacter (5.63%), and the relative abundance of the remaining bacteria is less than 5%. Among them, Microcystis is the most abundant bacterial group at three sampling points, and 67.59 Microcystis are identified as Microcystis aeruginosa (14.96%), while Microcystis aeruginosa is harmful algae in eutrophic fresh water, which may produce toxic cyanobacteria blooms, endangering aquatic organisms.

Test Example 2: Study of the Concentration Status and Potential Risks of Organic Toxics (Taking PAHs as an Example)

Through the in-situ monitoring at the water source in Wei Village by the present device for 30 days, the concentration and potential risks of organic toxics (taking PAHs as an example) in typical drinking water sources were obtained.

Experimental results analysis: Among the dissolved polycyclic aromatic hydrocarbons (PAHs) enriched by SPMDs in the water collection wells of Wei Village Water Plant, the detection frequency of lanthanum, fluoranthene and phenanthrene was the highest, and naphthalene and benzo[b]fluoranthene were detected occasionally. The total content of 16 PAHs enriched in SPMD was between 91 ng/g SPMD and 2196 ng/g SPMD. The time-weighted average concentration of 16 PAHs in water was between 0.7 and 6.5 ng/L. The sampling time through SPMDs technology is about 30 days, and the results have good time representativeness, high sensitivity, and are related to bioavailability.

It should be noted that the above embodiments are only used to illustrate the technical solutions of the present invention, and are not limited thereto; although the present invention has been described in detail with reference to the foregoing embodiments, those skilled in the art will understand that they can still. The technical solutions described in the foregoing embodiments are modified, or the equivalents of the technical features are replaced by the equivalents of the technical solutions of the embodiments of the present invention.

We claim:

1. An in-situ passive sampling device based on physical and chemical and bio-coupling monitoring, comprising an upper unit and a lower unit, the upper unit comprises a foam plastic tray (1) floating on a water surface, a bracket (2) on the foam plastic tray (1), and a power supply device (3) on the bracket (2), a microcontroller (4), a suction pump (5) and an automatic feeding box (6), the power supply device (3) supplies power to the suction pump (5) and the automatic feeding box (6) respectively, the microcontroller (4) is configured for timing switch control of the suction pump (5) and the automatic feeding box (6);

the lower unit comprises a support connecting device (7), a fish farming device (8), a sampling device (9), and the support connecting device (7) comprises a central post (71), a connecting rod (72), a feed pipe (73), a plastic hose (74), an upper surface of the central post (71) is connected to a lower bottom surface of the foam plastic tray (1) by a plurality of cables (10), and the central post (71) is internally provided with a longitudinal through passage (710), a lower end of the plastic hose (74) is screwed to an upper end of the through passage (710), an upper end of the plastic hose (74) extends upward and penetrates the foam plastic tray (1), and is connected to an outlet of the suction pump (5) and an outlet of the automatic feeding box (6) respectively through a manifold (11), an upper end of the feed pipe (73) is screwed to a lower port of the through passage (710), and a middle and lower portions of the feed pipe (73) is provided with external threads, the connecting rods (72) are provided in three in total, and proximal ends of the connecting rods (72) are detachably connected to side walls of the central post (71), respectively;

the fish farming device (8) comprises a fishbox body (81) and a fishbox cover (82), and the fishbox cover (82) and the fishbox body (81) are screwed to form a spherical structure, the fishbox cover (82) is provided with a thread hole (83) at a top, and a plurality of through holes (84) are provided around the thread hole (83), and the thread hole (83) is fitted with the external thread of the feed pipe (73), and an end of the feed pipe (73) is extended to an inner of the fishbox body (81), and fry (85) is inside the fishbox body (81), the sampling device (9) comprises a first fixing frame (91), a second fixing frame (92), a third fixing frame (93), the first fixing frame (91), a top of the second fixing frame (92), and the third fixing frame (93) are respectively connected to a respective distal end of each of the three connecting rods (72) by a respective lock (94), wherein the first fixing frame (91) is provided with a thin film diffusion gradient passive sampler (95), the second fixing frame (92) is provided with a semi-permeable membrane passive sampler (96), and the third fixing frame (93) is provided with a polar organic compound integrated sampler (97).

2. The in-situ passive sampling device according to claim 1, wherein the power supply device (3) comprises a battery (31), an inverter (32) and a solar panel (33), the solar panel (33) is obliquely placed on top of the bracket (2), and the inverter (32) is connected between the solar panel (33) and the battery (31) for converting direct current into alternating current, and the battery (31) is configured for supplying the stored alternating current to devices in need of power.

3. The in-situ passive sampling device according to claim 1, wherein the foam plastic tray (1) is made of PFU.

4. The in-situ passive sampling device according to claim 2, wherein a plurality of LED lamps (75) are embedded in a bottom of the central post (71).

5. The in-situ passive sampling device according to claim 4, wherein the central post (71) and the foam plastic tray (1) are provided with a waterproof cable (12) juxtaposed with the cable (10), the waterproof cable (12) is configured to electrically connect upwardly to the battery (31) and the microcontroller (4) and to supply power to the LED lamp (75) downward.

6. The in-situ passive sampling device according to claim 1, wherein the fishbox body (81) is provided at a bottom with a mesh (86), the mesh (86) includes a filler layer (87), and the filler layer (87) includes aquatic plants (88).

7. The in-situ passive sampling device according to claim 1, wherein a plurality of staggered strip grooves (89) are formed on a side wall of the fishbox body (81).

8. A method of using the in-situ passive sampling device according to claim 1, comprising biological monitoring of drinking water sources, the biological monitoring comprising biological community monitoring, toxicity testing, microbiological testing, and testing for contaminant residues in fish tissue.

* * * * *